(12) United States Patent
Agner

(10) Patent No.: US 6,245,238 B1
(45) Date of Patent: Jun. 12, 2001

(54) PURIFICATION OF PEPTIDES AND OLIGONUCLEOTIDES BY SAMPLE DISPLACEMENT CHROMATOGRAPHY PROCESS AND APPARATUS

(76) Inventor: Erik Agner, Svaneveien 19B, N-1187 Oslo (NO)

( * ) Notice: Subject to any disclaimer, the term of this patent is extended or adjusted under 35 U.S.C. 154(b) by 0 days.

(21) Appl. No.: 09/403,153

(22) PCT Filed: Apr. 16, 1998

(86) PCT No.: PCT/GB98/01109

§ 371 Date: Oct. 15, 1999

§ 102(e) Date: Oct. 15, 1999

(87) PCT Pub. No.: WO98/46623

PCT Pub. Date: Oct. 22, 1998

(30) Foreign Application Priority Data

Apr. 16, 1997 (GB) .................................. 9707696

(51) Int. Cl.[7] .................................................. B01D 15/08
(52) U.S. Cl. ..................... 210/635; 210/656; 210/198.2; 530/413; 530/417
(58) Field of Search .................................. 210/635, 656, 210/659, 198.2; 530/413, 417

(56) References Cited

U.S. PATENT DOCUMENTS

| | | | |
|---|---|---|---|
| 5,439,591 | * 8/1995 | Pliura | 210/635 |
| 5,545,328 | 8/1996 | Pliura | 210/635 |
| 5,605,623 | 2/1997 | Afeyan | 210/198.2 |

OTHER PUBLICATIONS

Hodges, R.S., et al.; *Multi–Column Preparative Reversed–Phase Sample Displacement Chromatograhpy of Peptides*, Journal of Chromatography, vol. 548, No. 1 / 02, pp. 267–280 (Jul. 12, 1991).

Newburger, J., et al.; *Utility of the Displacement Effect in the Routine Optimization of Separations by Preparative Liquid Chromatography*, Journal of Chromatography, vol. 523, pp. 63–80 (Dec. 1990).

Meyer, V.R., *Peak Purity, Yield and Throughput in Preparative Liquid–Chromatography With Self–Displacement*, Journal of Chromatography, vol. 592, No. 1–2, pp. 17–25 (Feb. 21, 1992).

* cited by examiner

*Primary Examiner*—Ernest G. Therkorn
(74) *Attorney, Agent, or Firm*—The Firm of Hueschen and Sage; G. Patrick Sage

(57) ABSTRACT

Sample displacement chromatography is performed at low operating pressures (less than 30 bar) and/or at high sample loading (in excess of 500 mg/cm$^2$ column area), with product recovery being effected in a non-gradient manner. The low operating pressures permit the use of simple and inexpensive apparatus. Non-gradient product recovery allows the desired product to be allowed in solutions with advantageously high concentration. Materials which may be purified include pharmaceuticals, pharmaceutical excipients, fine chemicals, biochemicals, X-ray contrast agents, chelating agents, peptides, proteins, oligonucleotides and vaccines. Apparatus embodiments include sample displacement chromatography apparatus comprising one or more ion exchange columns in direct combination with one or more desalting columns, and multicolumn chromatography apparatus permitting switching between a series separation mode and a parallel extraction mode.

16 Claims, 3 Drawing Sheets

PURIFICATION OF PEPTIDES AND OLIGONUCLEOTIDES BY SAMPLE DISPLACEMENT CHROMATOGRAPHY PROCESS AND APPARATUS

Reference to Related Applications

This application is a 371 of PCT/GB98/01109 filed Apr. 16, 1998.

This invention is concerned with chromatographic separation, more particularly with a new and improved method of sample displacement chromatography and applications thereof, as well as with apparatus useful in such methods.

During the last 10–15 years displacement chromatography has been suggested as a useful alternative to liquid chromatography using elution techniques. In elution chromatography, components of a sample are transported along stationary phase material, e.g. in a column, by a mobile solvent phase. The various components interact at different levels with the stationary phase material and are therefore separated into bands. Displacement chromatography, on the other hands, utilises as mobile phase a displacer solution which has higher affinity for the stationary phase material than do the sample components. In the case of column chromatography the sample components are thereby displaced and driven down the column ahead of the displacer front, competing for adsorption sites and separating into individual component bands as they proceed.

Whereas elution chromatography normally results in substantial dilution of the sample material, displacement chromatography permits recovery of sample components at significantly higher concentrations and generally makes more efficient use of the stationary phase material. Furthermore, the boundaries between individual component bands tend to be self-sharpening as a result of being driven by the sharp displacer front; the "tailing" of bands observed in elution chromatography is thus avoided. However, displacement chromatography does suffer the disadvantage that, to achieve optimum results, operating conditions such as the composition, concentration and flow rate of the displacer solution must be tailored specifically to individual sample types.

Sample displacement chromatography is a self-displacement technique which was first proposed by Hodges et al. [*J. Chromatogr.* 444 (1988), pp. 349–362] for preparative purification of peptides by reversed phase HPLC, and which does away with the need for an extraneous displacer solution. The peptide components are applied to the column input and themselves compete for binding sites on the stationary phase as they are washed through the column or series of columns by an appropriate solvent. The more strongly binding components bind first and displace less strongly binding components to further along the column(s). The components are therefore separated according to their different degrees of hydrophobicity/hydrophilicity and thus their affinity for the stationary phase material. In a representative example a short pre-column is used to trap impurities which are more hydrophobic than the desired sample component, this being retained in and saturating the main column, while the more hydrophilic impurities are further displaced and so are washed out of the main column. It is suggested that the size of the pre-column may be adjusted to match the amount of hydrophobic impurities present in a particular sample, whilst the size of the main column may be adjusted to ensure maximum product retention and outflow of hydrophilic impurities.

Curiously Hodges et al. subsequently use gradient elution to recover the desired product from the main column, so that the advantageous potential of displacement chromatography for yielding relatively high concentration product solutions is lost. This would suggest that the initial component separation was incomplete.

Veeraragavan et al. [*J. Chromatogr.* 541 (1991), pp. 207–220] report application of the Hodges technique to purification of proteins using high performance anion exchange chromatography columns. The apparatus used was a low pressure fast protein liquid chromatographic system and again gradient elution was employed; this was presumably felt to be necessary in light of the observation that peak overlaps were a problem in the primary separation procedure. One and two column systems are specifically described, the former being applicable on what are said to be the rare occasions where the desired product is either the most or least strongly binding component. The possibility of using a multi-column system "in which theoretically every component of the protein sample could be fixed to a column of the proper dimensions" is noted.

Multi-column HPLC systems for sample displacement chromatography have in fact been described by Hodges, inter alia in CA-A-2059114. A representative illustration shows the use of ten reversed phase HPLC columns or column segments connected in series for the purification of peptide samples; after the sample material has been loaded and distributed/separated over the train of columns, individual columns or segments may be eluted separately, without resort to gradient elution, the desired product component being recovered in substantially pure form from at least one such column or segment. Advantages of this process are said to be that (i) it allows ten-fold greater loading than comparable gradient elution separations; (ii) it involves minimal use of costly HPLC solvents; (iii) it requires minimal use of fraction analyses; (iv) it avoids the need to use displacer solutions during the actual separation; and (v) operating costs in terms of solvents, column packings and machine usage are much lower than typical gradient elutions.

The Hodges multi-column procedure does not appear to have been widely adopted and has been found in practice to give products with insufficient purity as a result of inadequate resolution of the product from closely related impurities. Moreover, by virtue of the need to operate HPLC procedures at high pressure, typically 80–200 bar, the apparatus required is necessarily complicated and expensive.

The present invention is based on the finding that efficient and reproducible separation of closely related sample components may be achieved using sample displacement chromatography at low operating pressures and recovering the desired product in a non-gradient manner. The use of low operating pressures greatly simplifies apparatus requirements, permitting the use of simpler and less expensive pumps, taps, connectors and the like than are required for HPLC systems; the consequential low mobile phase flow rates have been found to give rise to good separation of the sample components. By avoiding use of gradient elution the separation procedure also minimises solvent requirements and facilitates recovery of the desired product in an advantageously high concentration.

The procedure also makes optimum use of the stationary phase chromatographic material, since at the end of a sample displacement chromatography separation the entire length of the chromatography bed will typically be in active use. In HPLC separations, on the other hand, only a small part of the stationary phase participates in the separation process at any given time. Sample displacement chromatography therefore permits a 10- to 100-fold increase in capacity for a given stationary phase material compared to HPLC.

According to one aspect of the present invention there is provided a method of sample displacement chromatography which comprises (i) applying a multi-component sample to one end of a chromatography bed comprising stationary phase material having affinity for components of the sample, causing components of the sample to become distributed along the chromatography bed by passage over the bed of a non-eluting mobile solvent phase under an operating pressure not exceeding 30 bar, and (ii) recovering a desired component of the sample from at least a portion of the chromatography bed under steady state (i.e. non-gradient) processing conditions.

In general, it is preferred that the desired product should be the major component (e.g. at least 50%) of its type within the sample so that it will give rise to adequate displacement effects in respect of less strongly bound impurities, although less closely related products having substantially different chromatographic behaviour may be present in substantial quantities. The method is therefore suited to the purification of products from industrial scale syntheses, which typically will have been optimised to give yields well in excess of 50%; a wide range of products may be purified in this way, including pharmaceuticals, pharmaceutical aids such as excipients, fine chemicals, biochemicals, diagnostic agents such as X-ray contrast agents, chelating agents etc. The method is also particularly well suited to purification of peptides and oligonucleotides prepared by solid phase syntheses, where the desired product is typically obtained in 50–80% yield and is contaminated with a number of impurities having very closely related structures.

The sample may be applied to the chromatography bed in solid or liquid (e.g. solution) form or may be applied bound to or adsorbed on an appropriate solid phase material.

A variety of stationary phase materials may be employed in the method of the invention. The requirement that the material has affinity for components of the sample is to be interpreted as requiring that the material has specific sites which are capable of reversible interaction with components of the sample. Gel filtration media, in which samples interact with networks rather than actual sites, are therefore inappropriate, but systems which may be used include straight and reversed phase chromatography, ion exchange chromatography, hydrophobic interaction chromatography and affinity chromatography. Preferred embodiments of the invention include the use of reversed phase chromatography in the purification of peptides, the use of anion exchange chromatography in the purification of peptides, proteins, oligonucleotides, phosphosugars and a wide range of synthetic non-biomolecules containing impurities with different levels of charge from the desired product, and the use of affinity chromatography with phenyl boronic acid-containing chromatography beds in the purification of products containing cis-diols.

The use of sample displacement chromatography in the purification of oligonucleotides is itself new and constitutes a feature of the present invention. In many cases crude synthetic oligonucleotide products comprise a mixture of the desired full length material with impurities which are shorter fragments and therefore contain fewer charged phosphate units. Accordingly the desired product will bind more strongly to anion exchange materials than do the impurities, which will accordingly be displaced whilst the desired product is retained on the chromatography bed. Such oligo-nucleotides may therefore be simply and effectively purified using only a single column system.

Stationary phase materials used in separation processes according to the invention may be in any convenient form, for example as membranes, gels or microspheres, especially monodisperse microspheres, and will usually be packed into one or more columns. In some embodiments it may be advantageous to employ extended column systems having a relatively narrow cross-sectional area, e.g. having a length-:internal diameter ratio of at least 500:1, for example in excess of 750:1, preferably in excess of 1000:1, in order to maximise interaction of the sample-components with the stationary phase material. Such use of extended columns may simplify subsequent sampling since samples may be taken from easily defined positions within the column.

One useful column system of this type comprises a stationary phase-containing capillary tube of plastics material, for example having an internal diameter of 0.8 mm and an overall length of 1–2 meters. Following sample displacement chromatography in accordance with the invention, individual sample components may be obtained by cutting out selected parts of the tube and recovering bound component therefrom. Alternatively the is entire stationary phase material may be pushed out of the tube (e.g. by application of liquid pressure following removal of material-retaining end pieces) and separated into discrete portions, the desired product being recovered from appropriate selected portions. Systems of this type are particularly useful in small scale separations and in preliminary investigations of chromatographic behaviour performed in order to design a larger scale system.

A series of interconnecting column segments may similarly be used, with the desired product being recovered from one or more selected segments following chromatography. The individual segments may, for example, be in the form of discs comprising an outer ring of a plastics material such as polytetrafluoroethylene, stationary phase material being present in the annular space within each ring, for example held between appropriately positioned filter membranes. A plurality of such discs may be held together in sealing contact during sample displacement chromatography and thereafter separated to permit individual processing of one or more selected discs.

Alternatively the process may be performed using multi-column techniques. The various columns are preferably associated with appropriate taps or valves or the like so that they may be connected in series during the sample displacement mode separation process but may be extracted individually or simultaneously in parallel during the recovery step.

In such a system the columns may advantageously all be connected to one dual position valve configured such that in one position of the valve a mobile solvent phase may be passed through the columns in series, and in the other position an extraction solvent, displacer solution or the like may be fed through the columns in parallel to individual sample collecting means associated with each column. Such valves are novel and constitute a feature of the invention. They may, for example, comprise (i) a fixed part having inlet and outlet ports for the mobile phase, inlet and outlet ports for each of a plurality of columns and an extraction solvent/displacer solution outlet port for each of said columns, and (ii) a moveable part having an extraction solvent/displacer solution inlet port and linking means, e.g. appropriate channels, conduits and/or grooves, such that in a first position the mobile phase inlet port, column inlet and outlet ports and mobile phase outlet port are connected in series, and in a second position the extraction solvent/displacer solution inlet port is connected to each of the column inlet ports and each of the column outlet ports is connected to the extraction solvent/ displacer solution outlet port for that column.

In another advantageous form of apparatus according to the invention the individual columns are formed in a multicolumn block, for example an 8×12 block having a height of 5–30 mm and horizontal dimensions similar to a conventional 96-well microtitre plate. Such a block may be slidably positioned between opposing plates, said plates being perforated with holes and having channels in their block-adjoining faces such that in a first position of the block, a mobile phase may be fed via one of the plates so as to pass through the individual columns in series. In a second position of the block, however, an extraction solvent, displacer solution or the like may be fed via one of the plates so as to pass through the individual columns in parallel and out through holes in the other plate. The apparatus is conveniently positioned vertically, with the mobile phase being fed to either plate, the extraction solvent or displacer solution being fed to the top plate and the bottom plate being arranged such that the individual samples from each column are fed to separate microtitre plate wells.

It has been found that method of the invention permits the efficient separation of sample components at substantially higher loadings of sample per unit area of column than have hitherto been used. Hodges in CA-A-2059114 describes a peptide separation procedure using six series-connected 3 cm length×4.6 mm internal diameter HPLC columns and states that optimum separation is achieved with a sample loading of 24 mg, higher loads leading to some loss of the desired product. In this system the optimum 24 mg load corresponds to a load:area value of 145 mg/cm$^2$. However, use of load:area values in excess of 500 mg/cm$^2$ e.g. of at least 1000 mg/cm$^2$ and advantageously in the range 3000–7000 mg/cm$^2$, has been found to result in highly efficient separations; both low and high pressure sample displacement chromatography techniques using such load:area values represent a further feature of the present invention. It will be appreciated that the overall length of the column(s) will be selected to match the column capacity to the amount of sample applied, it being desirable in most embodiments of the invention that there is sufficient stationary phase material to bind substantially all the sample material.

The present process in practice also uses greater sample loadings per unit column volume than does the Hodges procedure. Thus Hodges' 3 cm length×4.6 mm internal diameter columns each have internal volumes of ca. 0.5 ml, so that application of a 24 mg optimum loading to a series of six columns corresponds to a load of 8 mg peptide per ml of stationary phase. The present process, on the other hand, operates successfully at loadings of 10–40 mg of samples such as peptides per ml of reversed phase stationary material and loadings of 50–100 mg of samples such as peptides, proteins and oligonucleotides per ml of ion exchange stationary material.

It will be appreciated that this use of high loadings to obtain high resolution separations, coupled with the high capacity of sample displacement chromatography separations, means that the method of the invention makes especially efficient use of stationary phase material in a particularly simple, convenient and inexpensive manner.

The requirement that the mobile solvent phase used in separation processes according to the invention is non-eluting is to be interpreted as indicating that the solvent is capable of transporting less-retarded sample components to the next available binding sites but has little or no ability to interfere with interactions between the dissolved sample components and the stationary phase material. A wide range of solvent systems may be used subject to this requirement. Aqueous systems useful in, for example, reversed phase and ion exchange chromatography include water, buffer solutions, solution of bases such as sodium hydroxide, ammonium bicarbonate or ammonium hydroxide, and solutions of acids such as acetic acid or trifluoroacetic acid.

The versatility of separation procedures according to the invention with regard to solvent system usage has a number of beneficial effects. In one advantageous embodiment of the invention a sample such as a peptide is obtained from a polymer support/synthesis resin, e.g. by based-induced cleavage, applied directly to the chromatography bed, and subjected to sample displacement chromatography using a solution of the base or other cleavage reagent as the mobile phase. This avoids the need for intermediate isolation of the cleavage product and permits simplified handling of the product and the use of simplified apparatus in which the solid phase synthesis system is directly coupled to the chromatography system. The invention may also permit the purification of products from solution phase synthesis system in similar manner.

In general, the mobile solvent phase will be applied until the sample has been distributed over at least a part, preferably substantially all, of the stationary phase material; in some embodiments it may be appropriate to allow less retarded components to be washed away from the chromatography bed. Application of the mobile phase may therefore, for example, be stopped (i) once a predetermined volume (e.g. 1–3 column volumes) of the mobile phase has been applied, (ii) when a particular component appears at the outlet end of the chromatography bed, or (iii) when washed out material ceases to appear at the outlet end of the chromatography bed.

As noted above, in low pressure separations in accordance with the invention, the mobile solvent phase is applied at a pressure not exceeding 30 bar, e.g. less than 15 bar, preferably less than 10 bar. Operating pressures of around 3 bar may advantageously be employed for commercial separations; overpressures as low as 0.5 bar have been found to give good separations. It may be appropriate to use even lower or no overpressure, depending on the nature of the chromatography bed. Thus, for example, where the bed comprises relatively coarse material, e.g. a coarse polymer gel, the mobile solvent phase may be capable of movement as a result of gravity and/or interaction with the bed material; in such embodiments it may be appropriate to apply a very low overpressure such as 0.1 bar to control rather than to drive the flow of mobile solvent phase.

The pressure source which drives the mobile solvent phase may advantageously be a pressurised gas such as nitrogen, thereby avoiding the need for mechanical pumps and consequently reducing the operating costs of the process.

Recovery of the desired product may be achieved by any appropriate method, for example by extraction into an aqueous solvent system or a non-aqueous solvent system (e.g. an organic solvent or supercritical carbon dioxide), by use of a displacer solution having higher affinity for the stationary phase material than does the sample (e.g. aqueous acetonitrile or acetic acid in the case of reversed phase chromatography or a salt solution in the case of ion exchange chromatography), by a decrease in salt concentration (e.g. in the case of hydrophobic interaction chromatography), or by pH change. The use of steady state conditions inherently permits the product to be obtained in more concentrated form than is possible using gradient elution and since the recovery procedure is totally independent from the separation procedure, the conditions for recovery may be optimised to ensure maximum efficiency of product release and maximum efficiency of use of solvents, displacer solutions etc. without in any way compromising the efficiency of the separation. It is accordingly possible to recover products in concentrations 10- to 100-fold higher than those which may be obtained with gradient elution.

The ability to extract products into solvents of choice is also advantageous in allowing recovery of products in stabilised form or in an optimum form for use in subsequent processing steps. Thus, for example, a protein may be extracted using buffer solution at a pH appropriate to maximise stability of the protein.

In embodiments of the invention in which salt solutions are used to displace products such as proteins or oligonucleotides, for example from ion exchange chromatographic media, the resulting product samples may advantageously be passed directly to individual desalting columns in order to remove the salt as part of the extraction process. Such use of ion exchange and desalting columns in combination is itself novel and constitutes a feature of the present invention.

An important advantage of separation processes according to the invention is that they may be scaled up in a reproducible and consistent manner simply by increasing the cross-sectional area of the column in direct proportion to the increase in sample loading. Thus, for example, separation of a 100 μl crude peptide sample on a 0.8 mm internal diameter column contained a reversed phase chromatography medium and separation of a 1.6 ml sample using a system of columns with internal diameters of 3.2 mm (i.e. a 16-fold increase in cross-sectional area) and containing the same chromatography medium gave substantially identical product profiles. Similarly, purification of the pharmaceutical excipient methoxy-polyethylene glycol phosphate using a 1.6 mm internal diameter anion exchange column was found to be reproducibly scaleable up by a factor of 1000 to a column system with 5 cm internal diameter. This reproducibility permits variables such as the nature and form of the stationary phase material and the nature, pH and linear flow rate of the mobile phase to be optimised in small scale experiments, whereafter the sample load and column area may be proportionally scaled up to levels appropriate for preparative/commercial separations. It should be noted in this context that where a constant pressure is employed to drive the mobile phase, e.g. a constant gas pressure or a mechanical pump providing a set pressure, use of such a constant pressure will give the same mobile phase linear flow rate whatever the cross-sectional area of the column(s) if other parameters are unchanged.

The reproducibility and therefore the predictability of separations according to the invention has the advantage that multiple separations run in parallel will generate consistent and predictable results; such procedures may therefore be used with minimum effort in the simultaneous purification of products from multiple synthesisers, for example such as are used in combinatorial chemistry. Such purifications may readily be operated independently of each other, for example by use of appropriate multiway valves etc.

In general, where a sample proves particularly difficult to separate, it may be subjected to a plurality of consecutive purification procedures in accordance with the invention, for example using cation exchange chromatography followed by anion exchange chromatography, anion exchange chromatography followed by reversed phase chromatography, or hydrophobic interaction chromatography followed by ion exchange chromatography. Such tandem purifications, e.g. in which one or more bound/adsorbed sample fractions obtained by the first method are further purified by the second method without intermediate isolation, may readily be performed with apparatus incorporating appropriate multiswitching valves.

The invention may advantageously be applied to situations in which macromolecules are modified and an improved purity profile is required for the product; this may, for example, occur in vaccine production or protein-protein conjugation. If a macromolecule shows high homogeneity according to a particular separation method and that method also shows high purity for a hapten, the method may be applied to the final discrimination between the various substitution levels obtained in a conjugation reaction. Representative examples of such embodiments include separation by anion exchange chromatography of a protein conjugated to a negatively charged small molecule, and separation by hydrophobic interaction chromatography of a protein-protein conjugate in which the two proteins differ in their chromatographic behaviour.

BRIEF DESCRIPTION OF THE DRAWINGS

In the accompanying drawings, which serve to illustrate the invention without in any way limiting the same.

DESCRIPTION OF THE PREFERRED EMBODIMENTS

Figure 1:
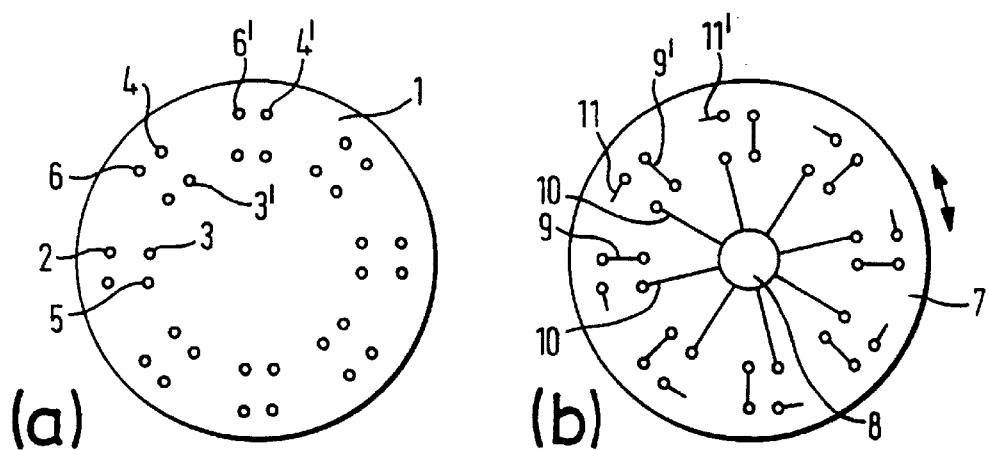
FIG. 1 is a schematic representation of a dual position valve useful in controlling multicolumn chromatographic apparatus in accordance with the invention.
Figure 1:
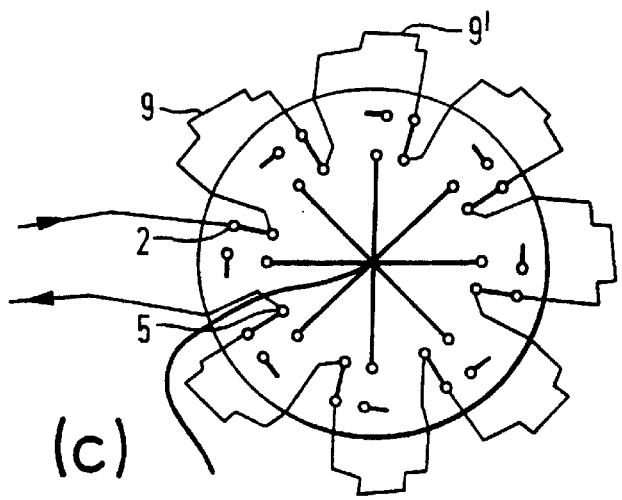
Figure 1:
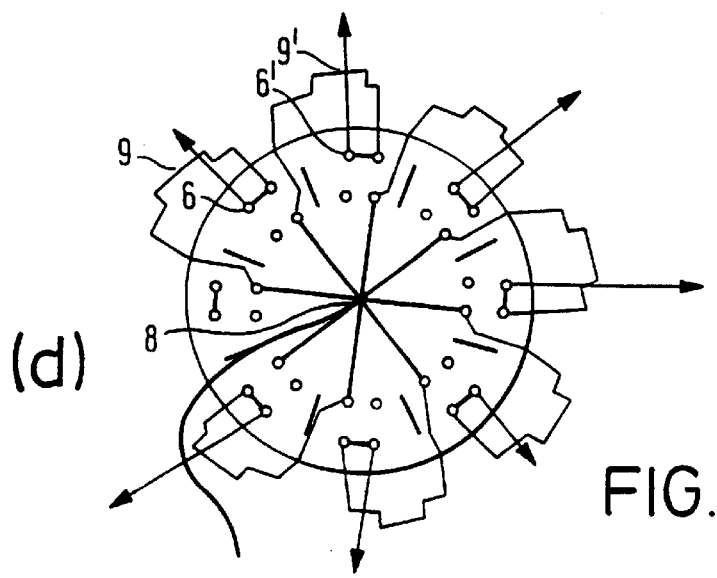

Referring to FIG. 1 in greater detail, (a) shows a fixed valve part 1 containing mobile phase inlet port 2, column inlet ports 3,3'. . . , column outlet ports 4,4'. . . , mobile phase outlet port 5 and extraction solvent/displacer solution outlet ports 6,6'. . . FIG. 1 (b) shows moveable valve part 7 containing extraction solvent/displacer solution inlet port 8, linking means 9,9'. . . permitting serial connection of ports 2,3,4,3',4'. . . ,5 in one position of said part 7, linking means 10,10'. . . permitting parallel connection of extraction solvent/displacer solution inlet port 8 and column inlet ports 3,3'. . . in the other position of said part 7, and linking means 11,11'. . . permitting connection of column outlet ports 4,4'. . . and extraction solvent/displacer solution outlet ports 6,6'. . . in said other position of said part 7. FIG. 1(c) illustrates serial flow of mobile phase from inlet port 2 through columns 9,9'. . . to outlet port 5. FIG. 1(d) illustrates parallel flow of extraction solvent/displacer solution from port 8 through columns 9,9'. . . to outlet ports 6,6'. . .

Figure 2:
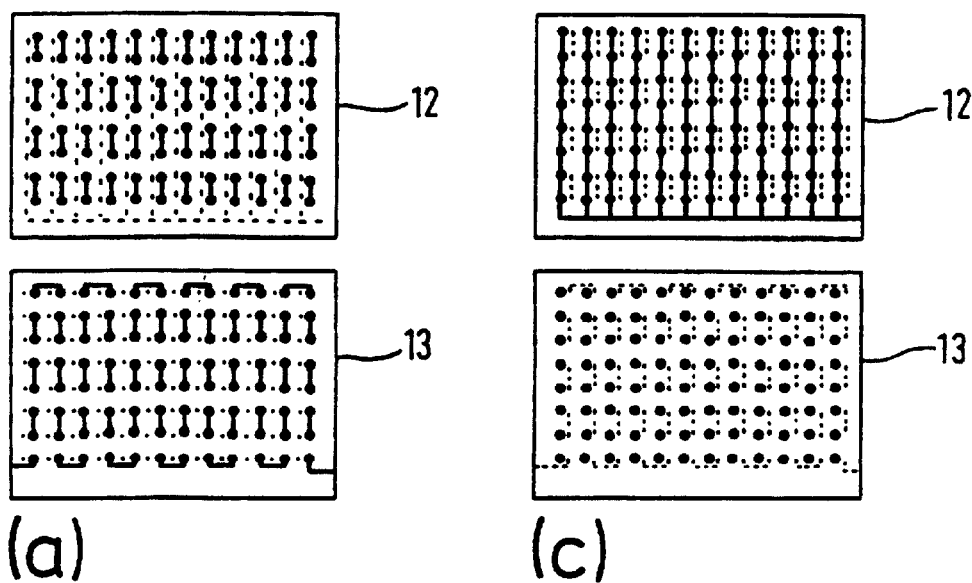
FIG. 2 is a schematic representation of a chromatographic apparatus in the form of a multicolumn block.
Figure 2:
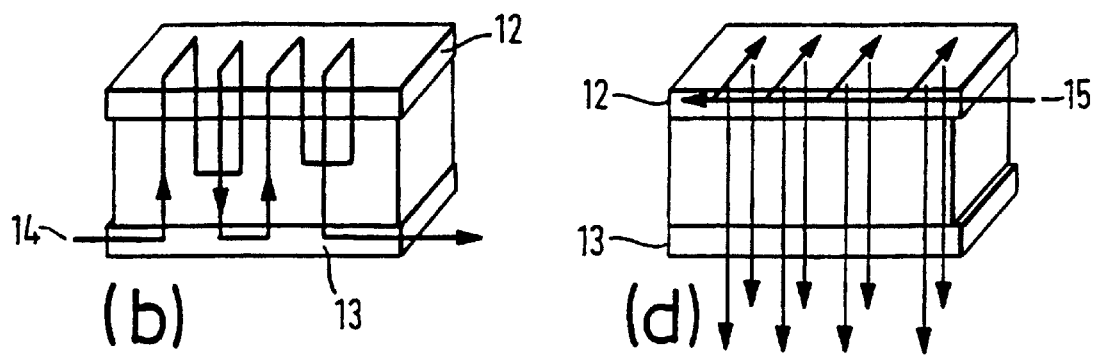

In FIG. 2, (a) shows a top plate 12 and bottom plate 13 adapted to contact an 8×12 multicolumn block assembly, with the channels used in serial separation mode shown in bold and the disconnected channels as broken lines. As shown in FIG. 2(b), mobile phase 14 is fed via the bottom plate 13 and passes through the columns in series. In FIG.

2(c) the channels and holes employed in parallel extraction mode are shown in bold and the disconnected channels as broken lines. As shown in FIG. 2(d) this configuration permits extraction solvent/displacer solution 15 to be fed via the top plate 12 through the columns in parallel.

The following non-limitative examples serve to illustrate the invention. Unless otherwise stated, analytical HPLC was performed using Beckman System Gold apparatus equipped with a 126 gradient pump, a 168 diode array detector, a 507 autosampler and System Gold software control.

EXAMPLE 1

Purification of Crude Peptide by Low Pressure Reversed Phase Sample Displacement Chromatography A crude sample of the decapeptide YADKITEDLK was prepared by solid phase synthesis using Fmoc protocol on a Biolynx 4070 automatic synthesiser, with 5- to 10-fold excesses of coupling reagents. The product was shown by HPLC analysis to have a purity of 65%.

The chromatography column comprised a 50 cm length× 1.6 mm internal diameter Teflon® tube fitted at its ends with appropriate frits and unions. The column was packed with 15 $\mu$m Resource RPC monodisperse particles (Pharmacia), applied as a slurry in methanol and subsequently equilibrated with 0.1% v/v aqueous trifluoroacetic acid (hereinafter 0.1% TFA).

A portion of the crude decapeptide (30 mg) was dissolved in 0.1% TFA (400 $\mu$l) and this solution was applied to the inlet end of the column. Further 0.1% TFA was applied under a gas pressure of 1.8 bar, resulting in a mobile phase flow rate of 10 $\mu$l/minute. After passage of 2 ml of 0.1 TFA the gas pressure was turned off, the bottom end piece was removed from the column and the stationary phase material was removed and divided into 75 equal sized portions using a Multiscreen filtration system (Millipore). The portions were each extracted with 10% v/v aqueous acetic acid to recover peptide sample fractions. HPLC analysis showed that the purity of the peptide in selected fractions had increased to 92%.

EXAMPLE 2

Comparison of Low Pressure Reversed Phase Sample Displacement Chromatography and Conventional HPLC in Purification of Crude Peptide The product investigated was a crude solid phase-synthesised peptide sample containing approximately 60% of the decapeptide YADKITEDLK together with at least three deletion sequences and a proportion of partially protected decapeptide.

A portion of this product (62 mg) was applied to a conventional 25 cm length×22 mm internal diameter preparative reversed phase HPLC column (Supelcosil C-18) and gradient eluted with 0.1% TFA: acetonitrile (5–15% v/v) at a flow rate of 10 ml/minute over a period of 60 minutes; separate fractions were collected for each minute of elution. After fraction analysis by HPLC eight fractions were combined and lyophilised to give 32 mg of decapeptide in 87% purity, corresponding to a yield of 75%.

A further portion of the crude product (25 mg, the calculated maximum column capacity) was applied to a chromatography column comprising a 2 m length×0.8 mm internal diameter Teflon® tube packed with 15 $\mu$m Resource RPC monodisperse particles as described in Example 1. 0.1% TFA was thereafter applied at a flow rate of 10 $\mu$l/minute until 2 $\mu$l thereof had been passed into the column, whereupon the flow was stopped. A succession of samples were then cut from both ends of the tube and extracted with 0.1% TFA:acetonitrile (50%); the extracts were analysed by HPLC. Once samples containing sufficiently pure decapeptide had been identified the remaining uncut tube was extracted in its entirety with 0.1% TFA:acetonitrile (50%); the resulting solution was lyophilised to give 10 mg of decapeptide in 90% purity, corresponding to a yield of 60%.

This confirms that low pressure sample displacement chromatography in accordance with the invention permits separation of a desired peptide from closely-eluting impurities with comparable efficiency to preparative HPLC techniques requiring substantially more complex equipment. The process of the invention also achieves a 10- to 100-fold reduction in organic solvent requirements, yields a more concentrated product solution and makes maximum use of the stationary phase material.

EXAMPLE 3

Scaling up in Purification of Crude Peptide by Low Pressure Reversed Phase Sample Displacement Chromatography In a small scale experiment a portion of a crude solid phase-synthesised YADKITEDLK decapeptide sample was purified as described in Example 1 except that (i) the column dimensions were 2 m length×0.8 mm internal diameter and (ii) 10 mM aqueous sodium bicarbonate was used in place of 0.1% TFA; the initial volume of the peptide solution applied to the column was 100 $\mu$l. The subsequent flow of aqueous sodium bicarbonate was maintained at a rate of 10 $\mu$l/minute and then stopped after 200 minutes, whereafter the stationary phase material was removed and divided into equal portions for analysis. Substantially pure product was found to occur in the samples obtained from between 20 and 60 cm from the column inlet; these samples were pooled, extracted and analysed by HPLC.

Figure 3:
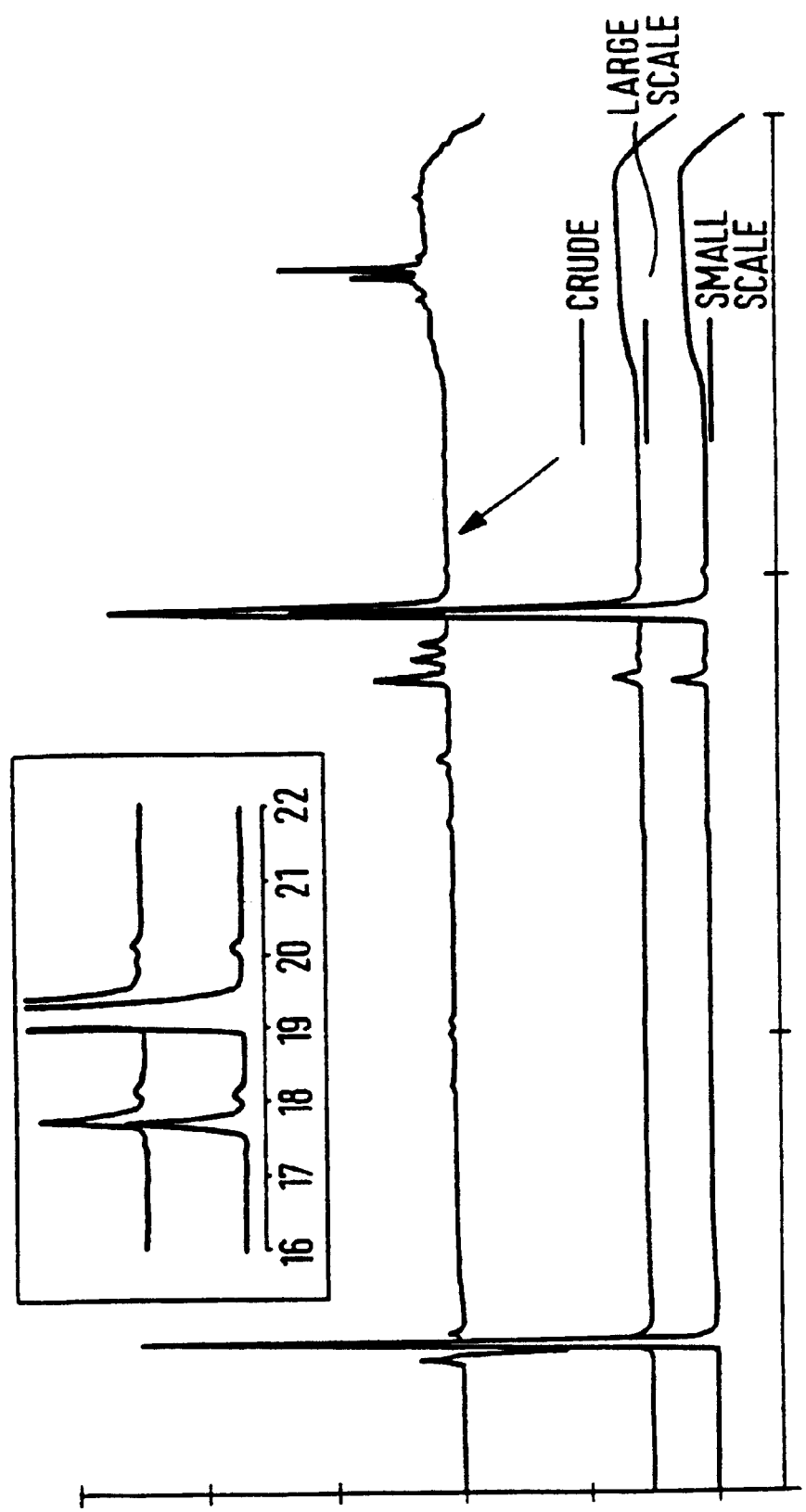
FIG. 3 is a chromatograph showing the reproducibility of sample displacement chromatography separations carried out at different scales.

A larger scale experiment utilised five 20 cm length×3.2 mm internal diameter columns similarly packed with 15 $\mu$m Resource RPC monodisperse particles and connected in series. To adjust for the 16-fold increase in column cross-sectional area the initial volume of peptide solution applied to the first column inlet was 1.6 ml; the flow rate of aqueous sodium bicarbonate was likewise increased to 160 $\mu$l/minute in order to maintain the same linear flow rate. After 200 minutes this flow was discontinued and the second and third columns (which correspond to the 20–60 cm from inlet part of the tube in the small scale experiment) were extracted together. The thus-obtained product was analysed by HPLC and found to exhibit a substantially completely identical chromatogram to the 20–60 cm product from the small scale experiment, as shown in FIG. 3 of the accompanying drawings.

EXAMPLE 4

Purification of Bacitracin by Low Pressure Cation Exchange Sample Displacement Chromatography Combined with Reversed Phase Sample Displacement Chromatography Commercially available bacitracin consists mainly of bacitracin A (ca. 40%) and the aminoacid-substituted analogues thereof bacitracin $B_1$, $B_2$, and $B_3$ (ca. 10–15% each);

the balance (ca. 20%) consists predominantly of other cyclic peptide variants and non-defined components.

Sepharose SP fast flow cation exchange material (Pharmacia) slurried in 20% v/v aqueous ethanol was packed into a 21 cm length×2.4 mm internal diameter Teflon® tube and equilibrated with 0.1% v/v aqueous acetic acid (hereinafter 0.1% AA). Bacitracin (100 mg) dissolved in 0.1% AA (1 ml) was then applied to the column, whereafter further 0.1% AA was applied at a flow rate of 50 $\mu$l/minute for 60 minutes, the back pressure from the column remained constant at 0.5 bar throughout this treatment. The stationary phase material was then removed from the column and divided into 24 equal portions using a Multiscreen filtration system; the portions were each extracted with pH 6.8 phosphate buffer containing 1 M sodium chloride to recover bacitracin fractions. HPLC analysis showed that fractions from the middle part of the column had increased purity, containing ca. 60% of bacitracin A and ca. 35% of bacitracin $B_1$–$B_3$; the nature of the remaining 5% of material was not investigated.

The above procedure was repeated, except that after the separation the column was cut at 6 and 14 cm from its inlet. The middle part of the column was then placed in front of a 50 cm length×1.6 mm internal diameter column similar to that described in Example 1 except that the reversed phase material therein had been equilibrated with 0.1% AA. 1 ml of 2 M sodium chloride in 0.1% AA was then applied to the resulting two column system, leading to displacement of bacitracin from the first column onto the second column, where a reversed phase sample displacement chromatographic separation took place. Division of the second column and extraction of appropriate parts thereof permitted recovery of salt-free product comprising ca. 75% of bacitracin A, ca. 20% of bacitracin $B_1$–$B_3$ and less than 5% of impurities.

EXAMPLE 5

Purification of Bovine Serum Albumin by Low Pressure Anion Exchange Sample Displacement Chromatography Eight 20 cm length×3.2 mm internal diameter columns were filled with Q Sepharose fast flow anion exchange material (Pharmacia) slurried in 20% v/v aqueous ethanol; the material was then equilibrated with pH 6.8 phosphate buffer. The columns were connected via two Omnifit 1164 valves such that they could be operated in series or in parallel.

With the columns connected in series, a solution of bovine serum albumin (Sigma A 2153—1.2 g) in pH 6.8 phosphate buffer (10 ml) was applied to the first column, whereafter further buffer was applied at a flow rate of 0.4 ml/minute for 100 minutes. The flow was then discontinued and the valves were switched so that each column was treated in parallel with pH 6.8 buffer containing 1 M sodium chloride at a flow rate of 0.5 ml/minute; the outflow from each column was passed through a Hitrap desalting column and collected in 1 ml fractions. In this way salt-free purified protein fractions were obtained at concentrations in excess of 100 mg/ml buffer; the total volume of buffer/solvent consumed during the process was less than 200 ml.

EXAMPLE 6

Isolation of Protein-Haptene Conjugates with Specific Substitution Levels

A protein material exhibiting homogeneous migration in anion exchange chromatography, for example as obtained in Example 5, was treated with the net negatively charged compound diethylene-triamine pentaacetic acid (activated by reaction of its triethylammonium salt with a subequimolar amount of diisopropylcarbodiimide in dimethylformamide). The agent was added to the protein solution in portions, and the course of the reaction was monitored by analytical anion exchange chromatography, which permitted identification of the various substitution levels.

Once a major portion of the protein was shown to be monosubstituted, the product mixture was separated by anion exchange sample displacement chromatography as described above, using a single 50 cm length×0.16 mm internal diameter column filled with the Q Sepharose material. The stationary phase material was then removed and divided into eight equal portions, which were extracted with 1 M sodium chloride solution and analysed.

Depending on the processing conditions and the particular chemistry used for modification, some 10–100 mg of homogeneous substituted protein may be obtained from this final separation. The simplicity of operation of separation procedures according to the invention, the high resolution achievable, the low solvent volume requirements and consequent high concentrations obtainable in respect of end product solutions, and the possibility of combining steps such as ion exchange chromatography and desalting, result in it being possible to carry out the entire procedure in a single day.

EXAMPLE 7

Purification of Oligonucleotide by Low Pressure Anion Exchange Sample Displacement Chromatography A solution of 25 mg of a crude solid phase-synthesised thiolated 21-mer oligonucleotide in concentrated aqueous ammonium hydroxide (the reagent used to cleave the oligonucleotide from the synthesis resin) was applied to the inlet end of a chromatography column comprising a 2 m length×0.8 mm internal diameter (i.e. 1 ml volume) Teflon® tube packed with 15 $\mu$m Q Sepharose fast flow anion exchange material equilibrated with concentrated ammonium hydroxide. Further concentrated ammonium hydroxide was then applied at a flow rate of 5 $\mu$l/minute for 400 minutes. Thereafter the flow was stopped, the outlet end filter was removed and the stationary phase material was pushed out and divided into twelve equal portions which were placed in filtering cups, water-washed and extracted with 10 mM sodium hydroxide solution containing 2 M sodium chloride to yield oligonucleotide sample fractions. The samples were desalted using NAP-10 columns (Pharmacia) and selected samples were analysed by capillary gel electrophoresis. Samples from the first quarter of the column contained 93–97% pure product, whereas samples from the second half were free of oligonucleotide material. Deletion sequences were found in samples from the intervening quarter of the column. Accordingly, since only about half of the stationary phase material was used in binding oligonucleotide material, a total of about 50 mg of the crude oligonucleotide per ml column volume may be separated using this system. The results indicated that at least 50% of the desired product could be recovered in 95% purity (as determined by capillary gel electrophoresis).

EXAMPLE 8

Purification of Methoxy-polyethylene Glycol Phosphate by Low Pressure Anion Exchange Sample Displacement Chromatography Methoxy-polyethylene glycol phosphate (MPP) is used as an excipient in pharmaceutical formulations and must therefore be prepared with a purity in excess of 98%. Impurities present in MPP as synthesised may include polyethylene glycol diphosphate, methoxy-polyethylene glycol, MPP monophenyl ester and MPP diphenyl ester. It is therefore desirable to perform a purification step after synthesis.

90% pure MPP (50 g) was dissolved in water (1 l) and the pH was adjusted to 8.8 by titration with concentrated ammonia. A sample of this solution (1 ml) was applied under a 3 bar pressure of nitrogen gas to a 1 m length×1.6 mm internal diameter Teflon® tube packed with Q Sepharose FF in the acetate form, and was followed by water (4 ml) under a similar 3 bar pressure. Sampling of the column contents (by GPC analysis with a TSK G3000SWXL column and using 5 mM phosphate. (pH 7) as the mobile phase) showed that the first 5 cm contained the stronger binding polyethylene glycol diphosphate along with MPP, whereas the last 20 cm contained MPP monophenyl ester along with MPP; the uncharged MPP diphenyl ester molecules were not retained and so passed straight through the column. The MPP content between 5 and 80 cm was extracted using 0.5 M hydrochloric acid and lyophilised to give dry MPP (38 mg). GPC and NMR analysis showed an impurity content of less than 1%.

This trial separation was then scaled up 1000-fold, using four 5 cm internal diameter columns packed with acetate form Q Sepharose FF to bed heights of 5, 25, 25 and 25 cm (total column volume 1.6 l), and applying 1 l of sample under a 3 bar pressure of nitrogen gas. A further 2 l of water were applied to distribute the sample along the length of the column system; the effluent from the column was found to contain the same components as the 80–100 cm portion of the column in the small-scale trial separation taken together with the material displaced from the column. Extraction of the three 25 cm columns as described above yielded MPP (37 g) in a solution volume of 1.3 l. GPC and NMR analysis showed a purity in excess of 99%.

EXAMPLE 9

Purification of N,N'-dipyridoxylethylenediamine-N'N-diacetate by Low Pressure Anion Exchange and Cation Exchange Sample Displacement Chromatography The chelating agent N,N'-dipyridoxylethylenediamine-N,N'-diacetate (PLED) is normally synthesised by alkylation of the corresponding diamine, e.g. using bromoacetic acid. Since the diamine contains at least four potential alkylation sites the synthetic product will inevitably possess a somewhat complex impurity profile, so that it is desirable to perform a purification step after synthesis.

Crude PLED was prepared by dissolving N,N'-dipyridoxylethylenediamine in aqueous sodium hydroxide at a concentration of ca. 25 g/l and adjusting the pH to 11. Aqueous bromoacetic acid (70% of the stoichiometric amount) was added to the solution and the pH was adjusted to 11.1. The resulting mixture was heated to 50° C. and the reaction was monitored by capillary electrophoresis (75 μm fused silica, 50 mM borate, pH 9.2, containing 1 mM diethylenetriamine pentaacetic acid). The reaction generated a mixture of monoalkylated, dialkylated and trialkylated products, in the ratio 1:2:1 as determined by UV absorbance at 214 nm. The yield of PLED was approximately 30%.

The reaction mixture was applied without work up to a column packed with Q Sepharose FF and separated using water as the mobile solvent phase (0.5 bar nitrogen pressure), thereby separating the components according to their substitution levels and leading to removal of lower charged impurities, which were displaced from the column. Following this separation, the column contained approximately 10 g/l material with an estimated product purity of 45% and quantitative recovery. The column was extracted using 1M acetic acid and applied directly to an SP Sepharose FF column at a loading of 50 mg/ml. Separation was effected using 1 M acetic acid as the mobile solvent phase (4 bar nitrogen pressure). Trialkylated impurities were displaced, whereas the dialkylated PLED product was recovered from the last part of the column in approximately 50% yield and with a purity of 93%. The first part of the column contained material that had not been displaced in the first purification step; some 25% of contaminated PLED product was found in the intermediate part of the column.

EXAMPLE 10

Purification of Iodixanol by Low Pressure Sample Displacement Borate Affinity Chromatography The X-ray contrast agent iodixanol is a dimer of two tri-iodinated aromatic rings. It contains four vicinal diol functions and therefore may be purified by affinity chromatography using resins containing phenyl boronic acid functions which coordinate cis-diols.

A crude sample of iodixanol (<80% purity) was dissolved in 0.1 M aqueous sodium carbonate and applied to a column packed with the phenyl boronic acid function-containing polyacrylamide gel Affi-Gel 601 (Biorad), at a loading of ca. 100 mg sample/mL gel. Further solvent was applied under a pressure of 0.1 bar nitrogen, at a flow rate of approximately 50 μl/minute. Flow was stopped after 90 minutes and the column was divided into six parts which were extracted using aqueous acetic acid. Analysis by reversed phase HPLC (Shimadzu LC-8, Brownlee C-18 column, 5–17% acetonitrile gradient over 20 minutes) confirmed the almost complete displacement of impurities and the isolation of product with over 93% purity and a yield in excess of 50%.

EXAMPLE 11

Purification of a Phosphosugar by Low Pressure Anion Exchange Sample Displacement Chromatography Vaccine structures based on chemical sequences from bacterial cell walls are synthesised as repeating units comprising carbohydrate phosphodiesters and, optionally, linking groups. Such a structure may be purified by applying 2 mg of a sample to a 20 cm length×0.5 mm internal diameter column packed with 15 μm Source Q anion exchange material (Pharmacia). After separation the column is divided into 1 cm portions which are extracted with 2 M aqueous sodium chloride and analysed by GPC (TSK G3000SWXL, 5 mM phosphate, RI detection). Earlier parts of the column show product with high purity, whilst additional peaks relating to shorter chain length compounds are observed in later parts of the column.

The purified product may be used for conjugation to macromolecules to obtain immune responses to hemofilus influenza virus B.

EXAMPLE 12

Purification of an Oligonucleotide Using an Anion Exchange Column Coupled to a Desalting Column Crude solid phase-synthesised oligonucleotide is obtained in concentrated aqueous ammonium hydroxide, the reagent used to cleave the oligonucleotide from the synthesis resin. The cleavage solution is applied directly at a loading of 50–100 mg/ml to an anion exchange resin equilibrated in concentrated ammonium hydroxide, and is separated using further concentrated ammonium hydroxide as the mobile solvent phase. This results in displacement of less charged impurities such as shorter failure sequences, leaving the desired oligonucleotide on the resin at a purity in excess of 95%. The resin is washed with water and extracted with 2 M aqueous sodium chloride. The saline extract is passed directly to a desalting column to separate the extracting salt from the oligonucleotide product; the latter product is thereby obtained in purified and highly concentrated form (50–100 mg/ml).

What is claimed is:

1. A method of sample displacement chromatography which comprises (i) applying a multi-component sample to one end of a chromatography bed comprising stationary phase material having affinity for components of the sample, causing components of the sample to become distributed along the chromatography bed by passage over the bed of a non-eluting mobile solvent phase under an operating pressure not exceeding 30 bar, and (ii) recovering a desired component of the sample from at least a portion of the chromatography bed under steady state processing conditions.

2. A method as claimed in claim 1 wherein the stationary phase material comprises straight phase, reversed phase, ion exchange, hydrophobic interaction or affinity chromatographic material.

3. A method as claimed in claim 2 wherein the stationary phase material comprises reversed phase chromatographic material and the sample comprises one or more peptides.

4. A method as claimed in claim 2 wherein the stationary phase material comprises anion exchange chromatographic material and the sample comprises one or more peptides, proteins or oligonucleotides.

5. A method as claimed in claim 1 wherein the stationary phase material is in the form of monodisperse microspheres.

6. A method as claimed in claim 1 wherein the mobile solvent phase is applied under an operating pressure not exceeding 15 bar.

7. A method as claimed in claim 6 wherein the mobile solvent phase is applied under an operating pressure not exceeding 10 bar.

8. A method as claimed in claim 7 wherein the mobile solvent phase is applied under an operating pressure of about 3 bar.

9. A method as claimed in claim 1 wherein the pressure applied to the mobile solvent phase derives from a pressurised gas.

10. A method as claimed in claim 1 wherein the stationary phase material is packed within one or more columns and the sample is applied in an amount exceeding 500 mg per square centimeter of the internal cross-sectional area of said column or columns.

11. A method as claimed in claim 10 wherein the sample is applied in an amount of at least 1000 mg per square centimeter of the internal cross-sectional area of said column or columns.

12. A method as claimed in claim 11 wherein the sample is applied in an amount of 3000–7000 mg per square centimeter of the internal cross-sectional area of said column or columns.

13. A method as claimed in claim 1 wherein the stationary phase material is packed within one or more columns such that the ratio of overall column length to column internal diameter is at least 500:1.

14. A method as claimed in claim 13 wherein said ratio is in excess of 750:1.

15. A method as claimed in claim 14 wherein said ratio is in excess of 1000:1.

16. A method as claimed in claim 1 wherein the desired component is recovered by application of a salt solution to at least a portion of the chromatography bed and the thus-obtained product is passed through a desalting column.

* * * * *